United States Patent [19]
Demyun et al.

[11] Patent Number: 5,100,318
[45] Date of Patent: Mar. 31, 1992

[54] ULTRASONIC METHOD AND APPARATUS FOR MEASURING THE PERIODONTAL POCKET

[75] Inventors: Stephen M. Demyun, Shavertown; Keith M. Hagenbuch, Waterford, both of Pa.

[73] Assignee: Periosonics, Inc., Shavertown, Pa.

[21] Appl. No.: 509,603

[22] Filed: Apr. 13, 1990

[51] Int. Cl.$^5$ .............................................. A61C 19/04
[52] U.S. Cl. ..................... 433/72; 433/215; 128/660.06
[58] Field of Search ............... 433/72, 75, 215, 141; 128/660.06, 660.1; 73/597

[56] References Cited

U.S. PATENT DOCUMENTS

| | | | |
|---|---|---|---|
| 4,494,548 | 1/1985 | Buon et al. | 128/660.1 |
| 4,501,555 | 2/1985 | Ditchburn | 433/72 |
| 4,530,362 | 7/1985 | Hetz | 128/660.1 |
| 4,754,760 | 7/1988 | Fukukita et al. | 128/660.06 |
| 4,764,114 | 8/1988 | Jeffcoat et al. | 433/72 |
| 4,913,157 | 4/1990 | Pratt, Jr. et al. | 73/597 |

FOREIGN PATENT DOCUMENTS 219988 4/1987 European Pat. Off. ........ 128/661.06

OTHER PUBLICATIONS

"The Use of Ultrasound for the Determination of Periodontal Bone Morphology", Palou et al., pp. 262-265, Periodontal Journal.

*Primary Examiner*—John J. Wilson
*Attorney, Agent, or Firm*—Neil F. Markva

[57] ABSTRACT

A noninvasive probe effects a method of measuring the depth of the periodontal pocket along an outer surface of a tooth wherein the depth is measured from an outer gum ledge tooth surface adjacent a tooth outer surface to the bottom of the pocket where the bone surface joins the tooth outer surface. The probe comprises an elongated handle portion, a neck portion and a head portion with each said portion having a respective longitudinal axis. The head portion includes an outer tip section and a transducer section connecting the tip section to the neck portion. The outer tip section includes a gum contacting end surface having a structural configuration effective to completely engage the outer gum ledge surface adjacent the tooth outer surface. The probe is used in combination with an assembly comprising a mechanism for establishing a first ultrasound pulse travel path having a fixed, reflective delay time and a second ultrasound pulse travel path having a variable, reflective delay time. The difference between the fixed, reflective delay time and the variable, reflective delay time is measured and then displayed to determine the depth measurement for the periodontal pocket.

21 Claims, 2 Drawing Sheets

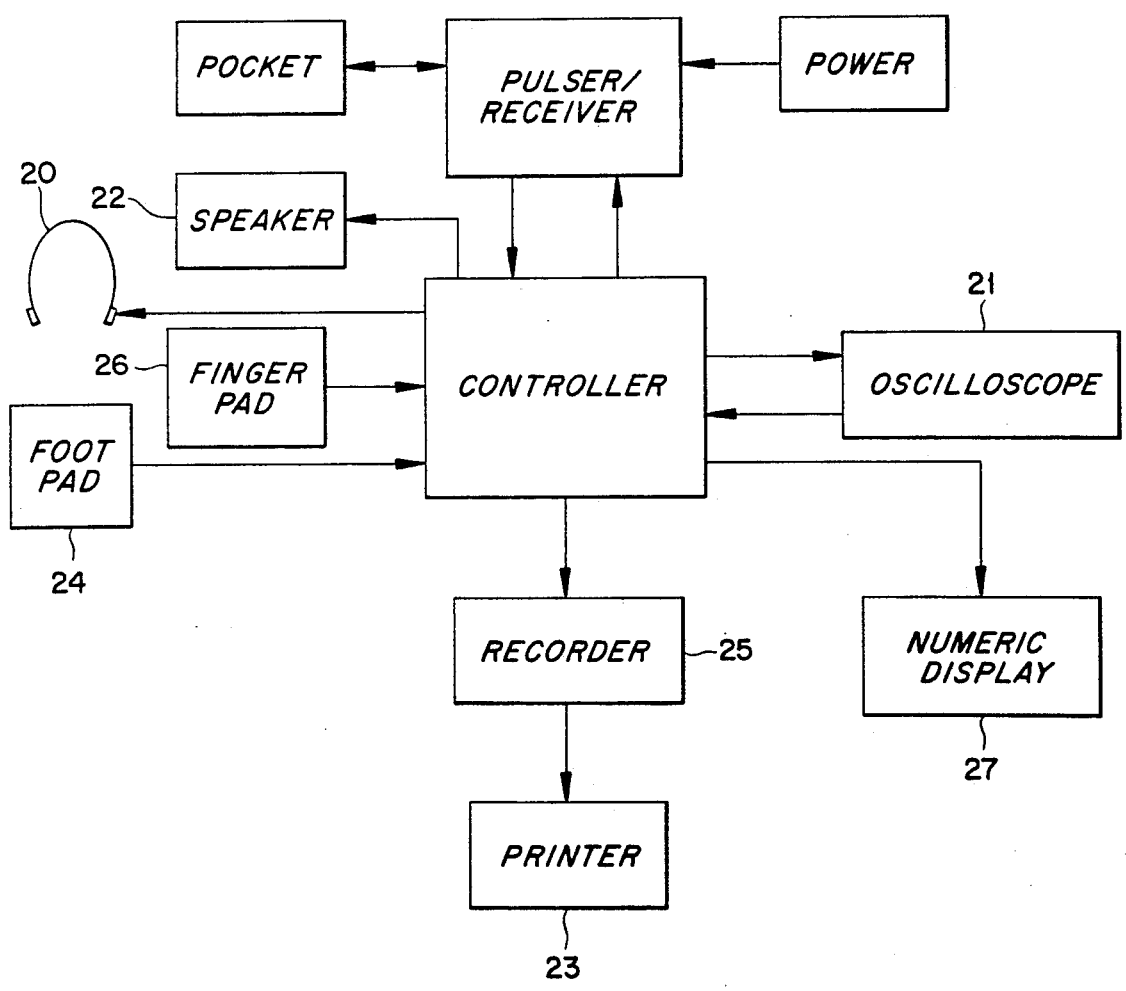

ULTRASONIC METHOD AND APPARATUS FOR MEASURING THE PERIODONTAL POCKET

FIELD OF THE INVENTION

This invention relates to the diagnosing of periodontal disease. More particularly, the invention relates to the non-invasive ultrasonic diagnosis of a periodontal disease condition in a mouth.

BACKGROUND OF THE INVENTION

A mechanical dental probe is now used to diagnose periodontal disease. The probe comprises a stainless steel instrument shaped to slide between a tooth and the gum with the probe tip diameter being about 0.7 of a millimeter (mm). Depending on the particular prior art probe being used, reference marks may occur along the length of the probe at depths of 3, 6, 8 and 10 mm or 1, 2, 3, 6, 8, and 10 mm. Due to a variety of factors, pocket depths are not reproducibly determined to a precision better than 0.5 mm.

A healthy gum tissue is firm, has a coral pink color and fits tightly to the teeth. Healthy gum tissue does not bleed when brushed, flossed or probed. The depth registered on the measuring probe for healthy gum tissue will be between 1 and 3 mm. This depth is the distance from the top of the gum surface to the attachment of periodontal ligament at its position relative to the alveolar crest.

The characteristics of the various phases of the gum disease periodontitis are well known as is the specific use of the stainless steel measuring instrument used to mechanically determine the depth of the periodontal cavity. An inflamed gum condition is called gingivitis where the gum tissue bleeds easily during brushing, flossing or probing and is characterized by being swollen, is red to purple in color and flaccid. The depth registered on the prior art measuring probe is still 1 to 3 mm.

In an early stage of periodontitis, the gum tissue condition is characterized by inflammation, loss of gum attachment and loss of bone support. The periodontal pocket depth is 3 to 5 mm with this early stage of periodontitis.

Finally, there is a moderate to advanced periodontitis condition in which the supporting gum and bone tissue have deteriorated and the tooth loosens. The periodontal cavity depth is 5 to 7 mm in moderate cases and greater than 7 mm in advanced cases. The free gingival margin may display a return to healthy appearance in these more advanced cases despite the continued bone loss.

With the prior art mechanical probe, a first set of measurements requires six measurements on each tooth, namely, one in each outer corner, one at the outer surface center, and a similar set on the inside outer surface of the tooth. For a patient with a full complement of 32 teeth, this requires 192 measurements. The dentist or technician may try to slide the probe along the outer surface of the tooth from one location to another without withdrawing the probe unless the patient complains about the discomfort. Each depth measurement must be recorded on an appropriate data sheet. Therefore, two people may be required to facilitate the taking of a set of measurements over the shortest time possible, i.e., one to make the measurements and the other to record them. Such a procedure may take up to about 20 minutes for each patient if properly performed.

Although ultrasound techniques have been used in medicine for years in the fields of obstetrics and ophthalmology, no viable ultrasound instrument exists for dental diagnostic purposes. Diagnostic ultrasound commonly uses the pulse echo technique for measuring distances. The reflected sound pulses are referred to as pulse echoes that return to the transducer where they are converted into electrical pulses which are displayed on a cathode ray tube as found in an oscilloscope.

Earlier attempts to use ultrasound pulses for measuring the depth of the periodontal pocket have failed. Therefore no ultrasonic procedure is available for replacing the often painful use of the mechanical measuring probe as described above. The earlier attempts at the use of ultrasound pulses to measure the periodontal cavity are described in an article entitled "The Use of Ultrasound for the Determination of Periodontal Bone Morphology" and found in the Apr., 1987 issue of *J. PERIODONTAL.* Page 262.

In accordance with the known ultrasonic procedure, an electrical pulse generator directs an electrical pulse to a transducer which changes the electrical pulse into a sound pulse. The transducer, in turn, directs the ultrasonic pulse to any desired surface where a pulse echo is reflected back to the transducer. The ultrasonic pulse echo is converted by the transducer to an electrical pulse for display on a cathode ray tube. The use of this technique, by itself, in the earlier ultrasonic periodontal diagnosing apparatus was found unsuccessful because the results were not accurately reproduced when compared to corresponding mechanical probe measurements.

It is difficult for one person to make a set of measurements along each tooth in a mouth for the purpose of diagnosing or tracking periodontal disease. As now practiced, the mechanical probe must be placed between the gum and the tooth, the measurement read along the edge of that probe followed by the recording of the reading. If one person is to do this, the probe must be removed from the mouth and placed down. A writing instrument then must be picked up and used. The same procedure must be repeated for each measurement. If a patient has a full complement of 32 teeth with six measurements for each tooth, this involves a full complement of 192 measurements, more than both the patient and the dentist could bear. Therefore, under normal circumstances, a technician records the readings called out by the dentist.

PURPOSE OF THE INVENTION

The primary object of this invention is to provide a non-invasive method and apparatus for measuring the depth of the periodontal pocket from the gum surface adjacent a tooth to the bone surface at the bottom of the pocket for diagnosing the dental condition in a mouth.

A further object of the invention is to provide an ultrasonic probe having a structural configuration effective to reproducibly and accurately measure the depth of a periodontal pocket around each tooth located in a mouth.

Another object of the invention is to provide an assembly for measuring the depth of the periodontal pocket along an outer surface of a tooth wherein it is possible for one person to effect a plurality of measurements.

SUMMARY OF THE INVENTION

The noninvasive method of the invention is directed to measuring the depth of a periodontal pocket from a gum surface adjacent a tooth to a bone surface at the bottom of the tooth for diagnosing the dental condition in a mouth. The method comprises establishing a first ultrasound pulse travel path having a fixed, reflected delay time and a second ultrasound pulse travel path having a variable, reflected delay time. The difference between the fixed, reflected delay time of a first ultrasonic echo pulse signal reflected at the gum surface and the variable, reflected delay time of a second ultrasonic echo pulse signal reflected from the bone surface at the bottom of the periodontal pocket is measured. A representation of this difference between the fixed, reflected delay time and the variable, reflected delay time is then displayed to determine the depth measurement for the periodontal pocket.

In a specific embodiment of the method, the ultrasonic travel path establishing step includes producing an initial ultrasonic pulse having a pulse length of about 0.5 mm directed to the gum surface through a fixed length outer tip section of a probe. The outer tip section has a gum contacting end surface for focusing the initial ultrasonic pulse to detect a periodontal pocket having a lateral dimension of about 1 mm or less.

A noninvasive probe used to effect the method of the invention comprises an elongated handle portion, a neck portion and a head portion with each of these portions having a respective longitudinal axis. The head portion includes an outer tip section and a transducer section connecting the tip section to the neck portion. The outer tip section includes a gum contacting end surface having a structural configuration effective to completely engage the outer gum ledge surface adjacent the tooth outer surface.

Sound transducing means disposed in the transducer section directs an ultrasonic sound pulse through the outer tip section toward the gum contacting end surface. The transducer means is effective to receive a reflected portion of the ultrasonic sound pulse from the contacting end surface at the gum surface and a second reflected portion of the ultrasonic sound pulse from the bone structure at the bottom of the periodontal pocket.

A particular feature of the probe structure is the disposition of the various portions with respect to each other. The longitudinal axis of the neck portion is disposed at an angle of about 90 degrees with respect to the longitudinal axis of the head portion and directed outwardly from a first side of the neck portion. The handle portion extends outwardly from one end of the neck portion and the head portion extends outwardly from the other end of the neck portion. The longitudinal axis of the neck portion is disposed at an angle of about 30 degrees with respect to the longitudinal axis of the handle portion which is directed outwardly from a second side of the neck portion opposite the first side of the neck portion. In a specific embodiment, the longitudinal axes of the handle, neck and head portions are disposed in a single plane.

Another feature of the probe is the structural configuration of the gum contacting end surface which is further effective to detect periodontal pockets having a predetermined lateral dimension. The end surface has a diameter of less than about 2 mm for detecting pockets having a lateral dimension of less than 2 mm. In a specific embodiment. the diameter of the end surface is about 1 mm.

An assembly of the invention comprises means for establishing a first ultrasound pulse travel path having a fixed, reflected delay time and a second ultrasound pulse travel path having a variable, reflected delay time. Means is provided for measuring the difference between the fixed, reflected delay time of a first ultrasonic echo pulse signal reflected from the gum surface and a variable, reflected delay time of a second ultrasonic echo pulse signal reflected from the bone surface at the bottom of the periodontal pocket. Display means is effective to display a representation of the difference between the fixed, reflected delay time and the variable, reflected delay time to determine the depth measurement for the periodontal pocket.

In a particular embodiment of the assembly, a probe includes transducer means and a gum contacting end surface effective to detect a preselected lateral size of a periodontal pocket. The transducer means is effective to provide a predetermined ultrasound pulse length equal to a preselected degree of resolution of probe transmission through gum tissue surrounding the tooth.

Another feature of the assembly is that it includes means for producing an ultrasound pulse from the transducer means at a power bandwidth in the range of from about 9 megahertz (MHz) to about 20 MHz. In a specific embodiment, the predetermined ultrasound pulse length is about 0.5 mm. The gum contacting end surface has a diameter in the range of about 1 mm to 2 mm. The transducer means is mounted in a head portion of the probe to send sound pulses to and receive echo pulses from the gum contacting end surface at the gum surface and from the bone at the bottom of the periodontal pocket. A visual display means is used for displaying the difference measurement representation resulting from the operation of the assembly.

In another embodiment of the assembly, the means for displaying the difference measurement representation includes recording means for reproducing a record of a plurality of measurements. Such recording means may include a memory for storing the plurality of measurements or a printer for producing a printed representation of the difference measurements. The difference measurement may be displayed on a cathode ray tube showing two separate pulses for each measurement including an initial ultrasound pulse from the transducer means and the echo pulse from the bone surface.

In a specific embodiment, means for monitoring the second ultrasound echo pulse signal reflected from the bone at the bottom of the cavity is provided. When that pulse is strongest, a switch means is provided for activating the recording means to produce a record of a depth measurement derived from the difference measurement representation based upon the echo pulse signal and selected through the use of the monitoring means The switch means may be either a foot-activated pad or a finger-activated pad mounted o the probe. The coordination of these various functions is effected by controller means such as a microprocessor or a standard programmable computer.

BRIEF DESCRIPTION OF THE DRAWINGS

Other objects of this invention will appear in the following description and appended claims, reference being made to the accompanying drawings forming a part of the specification wherein like reference characters designate corresponding parts in the several views.

FIG. 4 is a schematic flow diagram of an assembly made in accordance with the invention.

DESCRIPTION OF THE INVENTION

Figure 1:
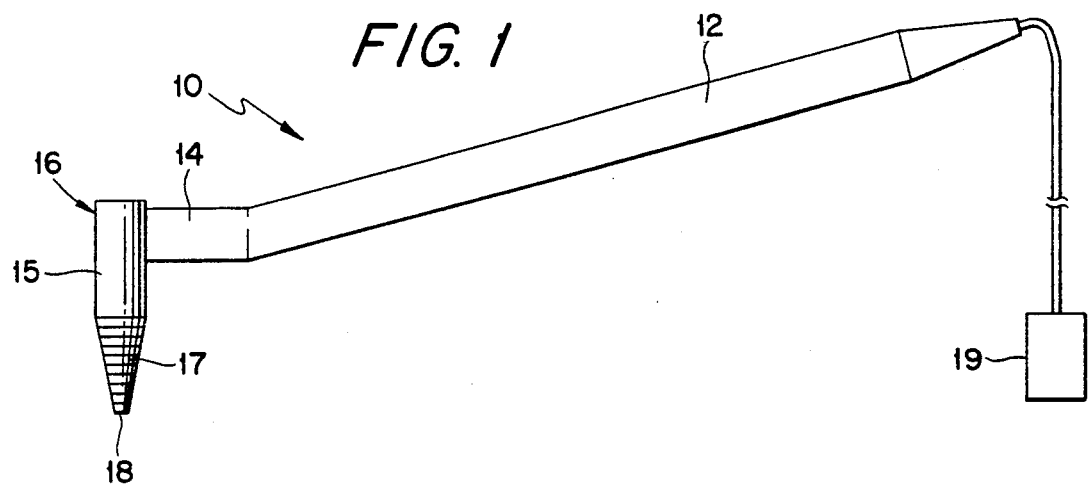
FIG. 1 is a schematic representation of a probe made in accordance with this invention.

The probe, generally designated 10, comprises an elongated handle portion 12, a neck portion 14 and a head portion 16 with each of the portions having a respective longitudinal axis. Head portion 16 includes an outer tip section 17 and a transducer section 15 connecting tip section 17 to neck portion 14. Outer tip section 17 includes a gum contacting end surface 18 having a structural configuration effective to completely engage the outer gum ledge surface adjacent the tooth outer surface.

A standard power supply 19 is used to energize a transducer means (not shown) housed in transducer section 15. In this embodiment, handle portion 12 is about 100 mm long, neck portion 14 is about 13 mm, head portion 16 about 20 mm, transducer section 15 about 11 mm and tip section 17 about 9 mm long.

Ultrasound energy is coupled from probe 10 to the gum tissue and reflected back rearwardly from the gum surface to probe 10 via intimate contact of probe end surface 18 with the gum surface. Unexpectedly, it has been found that significant energy is effectively lost to the measurement process if the entire end surface 18 does not completely engage the gum surface. Thus, it has been determined unexpectedly that end surface 18 must have a diameter of less than about 2 mm. In this specific embodiment, probe end surface 18 has a tip diameter of about 1 mm. Such a diameter provides an acceptable limitation on the lateral dimension of the ultrasound pulses emanating from end surface 18. Such narrow pulses will provide capability of detecting periodontal pockets of very small lateral dimensions less than about 1 mm.

Figure 3:
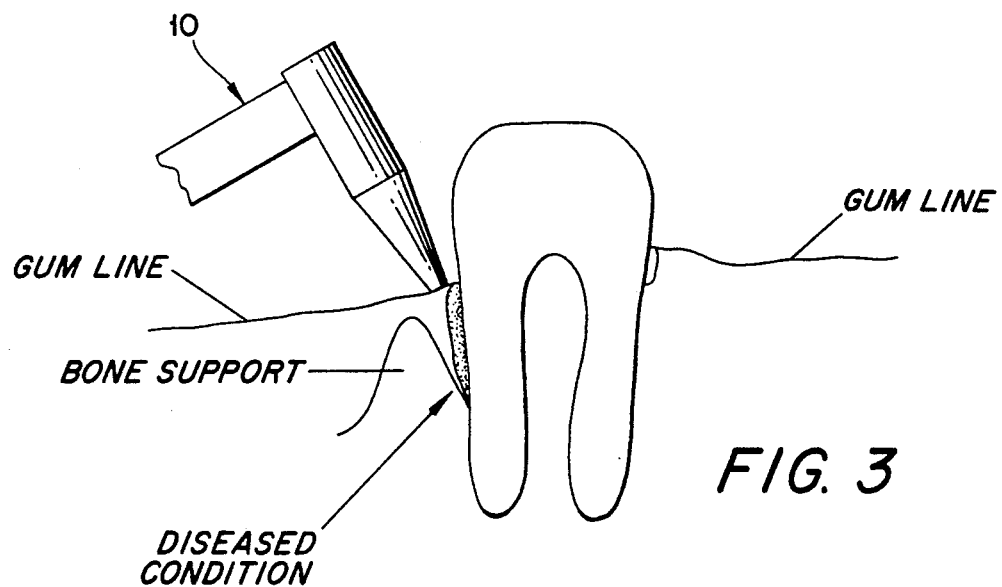
FIG. 3 is a diagrammatic view of a probe of the invention shown engaging the gum surface for effecting the method of the invention.

The transducing means housed in transducer section 15 produces ultrasound pulses which travel from end surface 18, through the gum to the supporting bone at the bottom of the pocket. Such pulses generally follow the dental probe path to the bottom of the periodontal pocket. FIG. 3 shows the disposition of probe 10 adjacent tooth and contiguously engaging the gum surface when measuring the depth of the periodontal pocket.

Upon reaching the bottom supporting bone, the ultrasound pulses will be reflected to form echo pulses which retrace the path back to probe end surface 18, and through outer tip section 17 back to the transducer. The sound velocity in gum tissue is about 1500 meters per second. The ultrasound pulses for this invention have been preselected to be about 0.5 mm in length to resolve the 0.5 mm depth variations obtained when using a mechanical probe according to prior art procedures. Dividing the pulse length by the sound velocity produces a pulse time length of about 0.33 microseconds.

It has been unexpectedly found that the selected degree of resolution of probe transmission through gum tissue surrounding the tooth requires a power bandwidth in the range of from about 9 MHz to about 20 MHz for producing an ultrasound pulse from the transducer means in transducer section 15.

Figure 2:
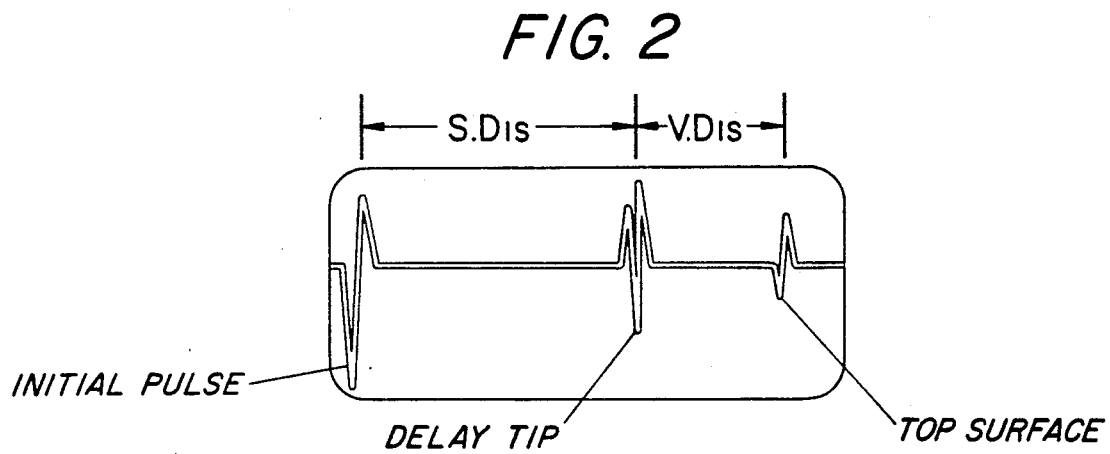
FIG. 2 is a diagrammatic representation of a pulse trace obtained through the use of a method conducted in accordance with the invention.

A typical pulse as visualized on a cathode ray tube of an oscilloscope is shown in FIG. 2. The initial impulse produced by the transducer is as shown. Outer tip section 17 measures 1 cm long from the transducer section 15 to end surface 18 in this embodiment and defines a delay line having a standard distance (S.Dis) corresponding to the length of the fixed, reflected delay time measured from the end surface 18 engaging the gum surface. The ultrasound pulses generated by the transducer travel down outer tip section 17 at the speed of sound which is about 1800 meters per second. A small portion of the energy of the ultrasound pulses is reflected from end surface 18 at the gum surface and returns to be received by the transducer in transducer section 15.

The remaining energy of the ultrasound pulse travels through end surface 18 into the gum tissue where it is attenuated before it reflects from the bone. Upon hitting the bone, an ultrasonic echo pulse travels back through the gum and into outer tip section 17 through end surface 18 to be received by the transducer. This distance between the delay tip peak and the top surface peak is the variable distance (V.Dis). The echo pulses received from end surface 18 contiguously engaged with the gum surface serves as a time reference. The delay time between the pulses of the delay tip peak and those pulses traveling through the tissue represents the travel time from the bone to the gum surface. Typical delay times are 4 microseconds for a 3 mm deep pocket and 8 microseconds for a 6 mm deep pocket.

Measurement results displayed on an oscilloscope cathode ray tube show the signal amplitude as a function of time which is displayed horizontally. In an actual reading under actual conditions, a set of decreasing reverberations occurs in the displayed traces because of the signal bouncing back and forth between the transducer and probe tip end surface 18. Noise is generally picked up from the reverberation within outer tip section 17 but the reflected echo pulse from the bone is clearly distinguishable from any of the other trace peaks.

The greater the disease condition, the larger will be the variable distance (V.Dis) shown in the results. This constitutes the difference between the fixed, reflected delay time of a first ultrasonic echo pulse signal reflected from the gum surface and a variable, reflected delay time of a second ultrasonic echo pulse signal reflected from the bone surface at the bottom of the periodontal pocket. Once this representation is made, the difference shown on the oscilloscope can be used to calculate the actual depth of the periodontal pocket.

FIG. 4 shows an assembly for effecting an automatic measurement of pocket depths which one person may operate. An ultrasonic pulser/receiver constituting a transducer mechanism is part of a probe made in accordance with the invention. A signal detector automatically recognizes the echo pulse returning from the bone at the bottom of the pocket and measures the difference of delay times between the echo pulse received from end surface 18 and the further echo pulse received from the bone structure. A representation as shown in FIG. 2 appears on oscilloscope 21. A controller such as a microprocessor directs the various signals to perform the method functions according to the invention.

The delay time is automatically converted into a depth measurement by multiplying one-half the delay time by the sound velocity in the tissue. The resultant value is then digitally displayed on the numeric display 27. Additionally, an audible prompt such as a set of earphones 20 or a speaker 22 may be used to monitor the signal being received from the bone echo pulse. Upon indicating a strong echo has been detected, a foot-activated pad 24 or a finger-activated pad 26 which might be mounted on probe 10 would be touched to automatically record in recorder 25 the digitally displayed depth of the periodontal pocket.

Where desired, the depth measurements may be automatically recorded in a memory capable of recording a plurality of such measurements. A printer 23 might be programmed through the use of a microcomputer to print marks or measurement values on a special form at the latest measurement location equal to the depth measured. Such an automatic system will produce a graphic display that will show at a glance where periodontal pockets of significant depths occur with the automatic recording of same in a memory such as a computer memory.

While the ultrasonic method and apparatus for measuring the periodontal pocket has been shown and described in detail, it is obvious that this invention is not to be considered as limited to the exact form disclosed, and that changes in detail and construction may be made therein within the scope of the invention without departing from the spirit thereof.

Having thus set forth and disclosed the nature of this invention, what is claimed is:

1. A noninvasive probe for measuring the depth of the periodontal pocket along an outer surface of a tooth wherein the depth is measured from an outer gum ledge surface adjacent the tooth outer surface to the bottom of said pocket where the bone surface joins the tooth outer surface, said probe comprising:
    a) an elongated handle portion, a neck portion and a head portion with each said portion having a respective longitudinal axis,
    b) said head portion including an outer tip section and a transducer section disposed along the head portion longitudinal axis with the transducer section connecting the tip section to the neck portion,
    c) the outer tip section including a gum contacting end surface having a structural configuration effective to completely engage the outer gum ledge on the gum surface adjacent either the outer surface or the lingual surface of the tooth,
    d) sound transducer means disposed in the transducer section for directing an ultrasonic sound pulse in a direction parallel to the head portion longitudinal axis through the outer tip section and then through the gum contacting end surface to said bone surface,
    e) said transducer means being effective to receive a first reflected portion of the ultrasonic sound pulse along the direction of the head portion longitudinal axis from the contacting end surface at the gum surface adjacent either the outer surface or lingual surface of the tooth and a second reflected portion of the ultrasonic sound pulse along said direction of the head portion longitudinal axis from the bone surface at the bottom of said pocket,
    f) the longitudinal axis of the neck portion is disposed at an angle with respect to the longitudinal axis of the head portion whereby the transducer means produces an electrical pulse in response to each of the reflected portions of the outwardly directed ultrasonic sound pulse and directs said electrical pulse in a direction toward the longitudinal axis of the handle portion which extends outwardly from a first side of the neck portion,
    g) the handle portion extends outwardly from one end of the neck portion and the head portion extends outwardly from the other end of the neck portion,
    h) the longitudinal axis of the neck portion is disposed at an angle with respect to the longitudinal axis of the handle portion which extends outwardly from a second side of the neck portion opposite said first side.

2. A probe as defined in claim 1 wherein
    the longitudinal axis of the neck portion is disposed at an angle of about 90 degrees with respect to the longitudinal axis of the head portion, and
    the longitudinal axis of the neck portion is disposed at an angle of about 30 degrees with respect to the longitudinal axis of the handle portion.

3. A probe as defined in claim 1 wherein
    the longitudinal axes of the handle, neck and head portions are disposed in a single plane.

4. A probe as defined in claim 1 wherein
    the gum contacting end surface has a diameter f less than about 2 millimeters.

5. A probe as defined in claim 4 wherein
    the diameter is about 1 millimeter.

6. A noninvasive probe for measuring the depth of the periodontal pocket along an outer surface of a tooth wherein the depth is measured from an outer gum ledge surface adjacent the tooth outer surface to the bottom of said pocket where the bone surface joins the tooth outer surface, said probe comprising:
    a) an elongated handle portion, a neck portion and a head portion with each said portion having a respective longitudinal axis,
    b) said head portion being disposed at an angle with respect to the neck portion and including an outer tip section and a transducer section, said outer tip and transducer sections being disposed along the head portion longitudinal axis with the transducer section connecting the tip section to the neck portion,
    c) the outer tip section including a gum contacting end surface having a diameter of less than about 2 millimeters and a structural configuration effective to completely engage the outer gum ledge surface adjacent the tooth outer surface,
    d) sound transducer means disposed in the transducer section for directing an ultrasonic sound pulse outwardly through the outer tip section toward the gum contacting end surface,
    e) said transducer means being effective to receive a first reflected portion of the ultrasonic sound pulse from the contacting end surface at the gum surface and a second reflected portion of the ultrasonic sound pulse from the bone surface at the bottom of said pocket,
    f) said transducer means being further effective to produce an electrical pulse in response to each of the reflected portions of the ultrasonic sound pulse, and
    g) means for receiving said electrical pulses from the transducer means to determine said depth being measured,
    h) the structural configuration of said gum contacting end surface is further effective to detect periodontal pockets having a predetermined lateral dimension.

7. A noninvasive method for measuring the depth of a periodontal pocket from a gum surface adjacent a tooth to a bone surface at the bottom of said pocket for diagnosing the dental condition in a mouth, said method comprising:
   a) providing transducer means positioned to produce an outgoing ultrasonic pulse for impinging directly on said gum surface to thereby establish a first ultrasound pulse travel path having a fixed, reflected delay time and a second ultrasound pulse travel path having a variable, reflected delay time,
   b) measuring the difference between said fixed reflected delay time of a first ultrasonic echo pulse signal reflected from the gum surface, and said variable, reflected delay time of a second ultrasonic echo pulse signal reflected from said bone surface at the bottom of the periodontal pocket, and
   c) displaying a representation of said difference between the fixed, reflected delay time and the variable, reflected delay time to determine the depth measurement for the periodontal pocket,
   d) said first and second ultrasonic travel path establishing step includes producing an initial ultrasonic pulse having a pulse length of about 0.5 mm directed to the gum surface through a fixed length outer tip section of a probe, and
   e) positioning said outer tip section having a gum contacting end surface to contact said gum surface with said contacting end surface for focusing said initial ultrasonic pulse to detect a periodontal pocket having a lateral dimension of about 1 mm.

8. An assembly for measuring the depth of a periodontal pocket from a gum surface adjacent a tooth to a bone surface at the bottom of said pocket for diagnosing the dental condition in a mouth, said assembly comprising:
   a) an elongated handle portion, a neck portion and a head portion with each said portion having a respective longitudinal axis,
   b) said head portion longitudinal axis being disposed at an angle with respect to the handle portion longitudinal axis and said head a portion including an outer tip section having a gum contacting end surface with a structural configuration effective to completely engage the outer gum ledge surface adjacent the tooth outer surface,
   c) transducer means located in said head portion for directing an ultrasonic pulse in a direction parallel to the head portion longitudinal axis toward said bone structure through said gum ledge surface,
   d) means located in said head portion for receiving a first ultrasound echo pulse signal having a first travel path and a second ultrasound echo pulse signal having a second travel path, and
   e) means for measuring a time difference between said first travel path for said first ultrasonic echo pulse signal reflected from the gum surface and said second travel path for said second ultrasonic echo pulse signal reflected from said bone surface at the bottom of the periodontal pocket.

9. An assembly as defined in claim 8 wherein
said transducer means for directing said ultrasonic pulse includes a probe having a gum contacting end surface disposed along said head portion longitudinal axis and being effective to detect a preselected lateral size of a periodontal pocket,
said transducer means being effective to provide a predetermined ultrasound pulse length equal to a preselected degree of resolution of probe transmission through said gum surface and gum tissue surrounding the tooth.

10. An assembly as defined in claim 9 wherein
said transducer means produces an ultrasound pulse at a power bandwidth in the range of from about 9 MHz to about 20 MHz.

11. An assembly as defined in claim 9 wherein
the predetermined ultrasound pulse length is about 0.5 mm.

12. An assembly as defined in claim 9 wherein
the gum contacting end surface has a circular shape with a diameter in the range of about 1 mm to about 2 mm.

13. An assembly as defined in claim 9 wherein
said means for measuring includes means for displaying the time difference measurement representation,
said means for displaying having a visual display means.

14. An assembly as defined in claim 8 wherein
said means for measuring includes means for displaying a representation of said time difference between the first travel path and the second travel path to determine the depth measurement for the periodontal pocket.

15. An assembly as defined in claim 14 wherein
the means for displaying the time difference measurement representation includes recording means for producing a record of a plurality of measurements.

16. An assembly as defined in claim 15 wherein
the recording means includes a memory for storing said plurality of measurements.

17. An assembly as defined in claim 15 wherein
the recording means includes a printer for producing a printed representation of the time difference measurement.

18. An assembly as defined in claim 14 wherein
the means for displaying the time difference measurement representation includes recording means for producing a record of a plurality of measurements, means for monitoring the second ultrasonic echo pulse signal reflected from the bone at the bottom of the cavity, and switch means for activating the recording means to produce a record of a depth measurement derived from the time difference measurement representation.

19. An assembly as defined in claim 18 wherein
the switch means is a foot-activated pad.

20. An assembly as defined in claim 18 wherein
the switch means is a finger-activated pad mounted on the probe.

21. A noninvasive method for measuring the depth of a periodontal pocket from an outer gum ledge surface adjacent a tooth to a bone surface at the bottom of said pocket for diagnosing the depth of any periodontal pocket which may exist in a mouth, said method comprising:
   providing a noninvasive probe having a handle portion, a neck portion and a head portion with each said portion having a respective longitudinal axis, said head portion longitudinal axis being disposed at an angle with respect to the neck portion longitudinal axis and including transducer means located in the head portion for producing an outgoing ultrasonic pulse directed in a single direction for impinging directly on the outer gum ledge surface, b) providing the head portion with a gum contacting end surface having a structural configuration effective to completely engage the outer gum ledge surface, c) engaging the outer gum ledge with the ultrasonic pulse producing means and directing an outgoing ultrasonic pulse with the transducer means and from the gum contacting end surface through said outer gum ledge surface toward said bone structure, d) receiving a first ultrasound echo pulse signal reflected from said gum surface and a second ultrasound echo pulse signal reflected from said bone structure for each outgoing ultrasonic pulse impinging on the outer gum ledge surface, e) said first echo pulse signal having a fixed, delay time and said second echo pulse signal having a variable, delay time, f) measuring the time difference between said fixed, delay time of the first echo pulse signal, and said variable, delay time of the second echo pulse signal to determine the depth measurement for a periodontal pocket, g) said measuring step including converting the first and second echo pulse signals to first and second electrical signals, h) processing said electrical signals to produce a representation of said time difference representing said depth measurement, and i) recording said time difference representation in a memory means for a plurality of depth measurements.

* * * * *